United States Patent [19]

Hodgson, Jr.

[11] 4,431,662

[45] Feb. 14, 1984

[54] 1-(1,3-BENZODIOXOL-5-yl)-2-PYRROLIDINONE AND ITS MEDICINAL USE

[76] Inventor: Gordon L. Hodgson, Jr., 115 Radcliff Cir., Durham, N.C. 27713

[21] Appl. No.: 353,007

[22] Filed: Feb. 26, 1982

[30] Foreign Application Priority Data

Mar. 6, 1981 [GB] United Kingdom ............... 8107090

[51] Int. Cl.$^3$ ................... C07D 405/02; A61K 31/40
[52] U.S. Cl. ..................................... 424/274; 548/543
[58] Field of Search ...................... 548/543; 424/274

[56] References Cited

U.S. PATENT DOCUMENTS

| 4,110,105 | 8/1970 | Tesch | 71/95 |
| 4,239,770 | 12/1980 | Kyburz et al. | 424/274 |
| 4,263,038 | 4/1981 | Thiele | 71/92 |

FOREIGN PATENT DOCUMENTS

| 22737 | 1/1981 | European Pat. Off. |
| 2431489 | 2/1980 | France |

Primary Examiner—Paul M. Coughlan, Jr.
Assistant Examiner—D. B. Springer
Attorney, Agent, or Firm—Donald Brown

[57] ABSTRACT

This invention relates to the compound of formula (I), 1-(1,3-benzodioxol-5-yl)-2-pyrrolidinone, its preparation; its use in medicine for treatment of pain, inflammation and fever; and pharmaceutical formulations containing it.

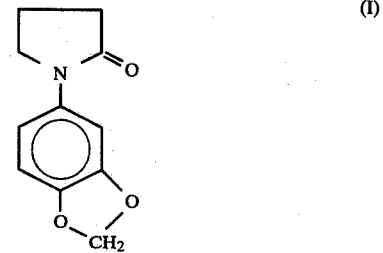

(I)

16 Claims, No Drawings

1-(1,3-BENZODIOXOL-5-YL)-2-PYRROLIDINONE AND ITS MEDICINAL USE

This invention relates to a compound useful in medicine, to the synthesis of the compound, to pharmaceutical formulations containing the compound and the preparation of such formulations, and to the use of the compounds in medicine.

We have found that the compound of formula (I),

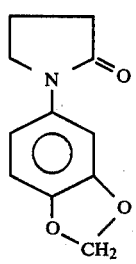

(I)

which is chemically named 1-(1,3-benzodioxol-5-yl)-2-pyrrolidinone is of value in medicine in the treatment or prophylaxis of pain, inflammation or fever. The compound of formula (I) hereinafter known as "compound (I)"; "active ingredient", or "active compound", has been found to have mild to moderately strong analgesic activity.

As an analgesic agent compound (I) is superior to acetaminophen and the prostaglandin synthetase inhibitors such as aspirin and zomepirac as shown in the trypsin assay but less active than the opiates such as codeine or morphine. However, the analgesic mode of action of the compound (I) is believed to be unlike that of codeine or morphine since its analgesic activity is not inhibited by naloxone, and it does not bind to the morphine receptor. Thus, compound (I) is considered non-narcotic. The duration of analgesic action is significantly greater for compound (I) than for codeine or morphine.

Compound (I) has also been found to have potent, long-lasting acute anti-inflammatory activity in the rat as shown in the carrageenan pleurisy assay (Vinegar et al., Proc. Soc. Exp. Biol. Med. 151, 556, (1976). Compound (I) resembles acetaminophen in its acute anti-inflammatory action but it has been found to be more potent and to have a longer-lasting anti-inflammatory effect at comparable dose levels.

Compound (I), like acetaminophen, has also been found to have antipyretic activity as shown by the yeast-induced hyperthermia assay in the rat (Khalili-Varasteh et al., Arch. Int. Pharmacodyn., 219, 149–159 (1976)). This is to say, the compound of formula (I) combats fever in the rat as does aspirin and acetaminophen.

Compound (I) may be used in the relief, treatment or prophylaxis of pain (moderate to severe), inflammation or fever, in a mammal, including man, such as: that resulting from headache, toothache, pain following general dental procedures, oral and general surgery, dysmenorrhea, myalgia, pain of unresectable cancer, joint and peripheral nerve disorders, rheumatoid arthritis, rheumatoid spondylitis, osteoarthritis, gouty arthritis and other arthritic conditions, pyresis and other conditions associated with pain, inflammation and fever.

The amount of the active compound, i.e. compound (I), required for use in the above conditions will, of course, vary both with the route of administration, the condition under treatment, and the mammal undergoing treatment, but is ultimately at the discretion of the physician. However, a suitable analgesic, anti-inflammatory and/or anti-pyretic dose of the active compound for a mammal is in the range of from 1 to 120 mg per kilogram bodyweight per day; a typical dose for a human recipient being 15 mg/kg body weight per day.

The desired dose is preferably presented as between two and four subdoses administered at appropriate intervals throughout the day. Thus where three sub-doses are employed each will lie in the range of from 1 to 20 mg (base)/kg body weight; a typical dose from a human recipient being 3 mg (base)/kg body weight.

While it is possible for the active compound to be administered alone as the raw chemical, it is preferable to present the active compound as a pharmaceutical formulation. Formulations of the present invention, both for veterinary and for human medical use, comprise the active compound together with one or more pharmaceutically acceptable carriers thereof and optionally any other therapeutic ingredients. The carrier(s) must be pharmaceutically acceptable in the sense of being compatible with the other ingredients of the formulation and not deleterious to the recipient thereof. The other therapeutic ingredient(s) may include other analgesics, anti-inflammatories or anti-pyretics.

The formulations include those suitable for oral, rectal or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught. The active compound may also be presented as a bolus, electuary or paste.

A tablet may be made by compression or moulding, optionally with one or more accessory ingredients. Compressed tablets may be prepared by compressing in a suitable machine, the active compound being in a free-flowing form such as a powder or granules, optionally mixed with a binder, lubricant, inert diluent, surface active or dispersing agent. Moulded tablets may be made by moulding in a suitable machine, comprising a mixture of the powdered active compound with any suitable carrier.

A syrup may be made by adding the active compound to a concentrated, aqueous solution of a sugar for example sucrose to which may also be added any accessory ingredient. Such accessory ingredient(s) may include flavourings, an agent to retard crystallization of the sugar or an agent to increase the solubility of any other ingredient, such as a polyhydric alcohol for example glycerol or sorbitol.

Formulations for rectal administration may be presented as a suppository with a usual carrier such as cocoa butter.

Formulations suitable for parenteral administration conveniently comprise a sterile aqueous preparation of the active compound which is preferably isotonic with the blood of the recipient.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

Compound (I) may be prepared by any method known in the art for the preparation of compounds of analogous structure.

(1) A method for preparing compound (I) comprises cyclisation, as hereinafter described, of a compound of formula (II) or a compound of formula (III):

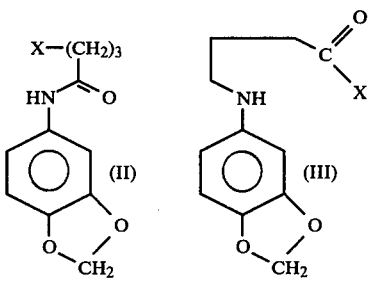

wherein X is a standard leaving group (J. March, Advanced Organic Chemistry, 2nd Ed., page 187, New York (1977)) such as halide for example chloride or bromide, hydroxide, —$OR^1$, imidazolyl, sulphoxonium or tosyl; and $R^1$ is hydrogen or alkyl of 1 to 4 carbon atoms, preferably ethyl. Preferred compounds of formula (II) are those wherein the leaving group is a halide (such as chloride or bromide), hydroxide or tosyloxy, and preferred compounds of formula (III) are those wherein the leaving group is —$OR^1$ as defined. A particularly preferred method comprises cyclisation of a compound of formula (II) as hereinbefore defined, especially wherein X is chloride.

Cyclisation may be effected at room temperature or with heating for example at a temperature of 155°-220° C., optionally in an oxygen-free atmosphere for example in nitrogen, optionally in an inert solvent such as tetrahydrofuran, dichloromethane, diethyl ether, tert-butanol, xylenes, or toluene, and optionally with a catalyst. The catalyst chosen will depend on the compound of formula (II) or (III) to be cyclised, for example, where the reaction involves elimination of an acid such as hydrochloric, a basic catalyst may be used with or without a solvent such as water or an alcohol such as butanol optionally, but preferably, in the presence of a phase transfer catalyst such as triethylbenzyl ammonium chloride with or without a solvent such as dichloromethane, diethyl ether, xylenes or toluene, but preferably dichloromethane. Examples of suitable basic catalysts are: an alkali metal hydride, hydroxide or alkoxide such as potassium or sodium hydride, potassium or sodium hydroxide, potassium tert-butoxide or lithium di-isopropylamide. The most preferred method of cyclisation is effected by using aqueous sodium hydroxide in the presence of triethylbenzyl ammonium chloride at room temperature.

Where X is a slow or poor leaving group cyclisation may take place by conversion in situ to a further or better leaving group. For example where X is hydroxide, tosyl chloride may be present in the reaction mixture in order that the tosyloxy group (a better leaving group) is substituted for the hydroxide group thereby causing cyclisation to proceed faster and more completely.

(2) A further method comprises reduction of a corresponding oxidised precursor of a compound of formula (I). For example, reduction of N(1,3-Benzodioxol-5-yl)succinimide (formula (IV)):

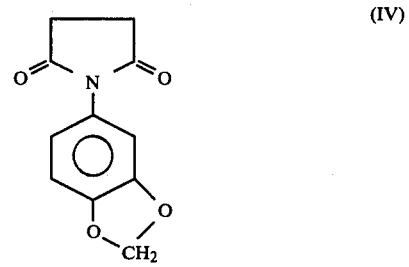

The reducing agent employed may be selected from those known to persons skilled in the art, such as lithium aluminium hydride, di-iso-butyl aluminium hydride, diborane or a lithium trialkyl borohydride (wherein the alkyl moiety has from one to four carbon atoms) in an inert solvent such as tetrahydrofuran and sodium borohydride in dilute mineral acid for example hydrochloric acid.

A compound of formula (II), (III) or (IV) may itself be prepared by analogous methods known to those skilled in the art, for example, by reacting 3,4-methylene dioxyaniline (formula (V)):

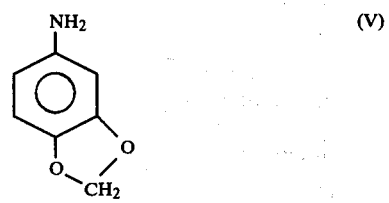

or a salt thereof such as an acid addition salt thereof for example the hydrochloride or an alkali metal or alkaline earth metal salt thereof for example the lithium salt, with an internal ester, acid halide for example acid chloride, or acid anhydride. For example, the compound of formula (V) maybe reacted with Cl—$(CH_2)_3$—COCl to produce a compound of formula (II) wherein X is chloride in the presence of triethylamine in dimethoxyethane or dichloromethane.

The reaction may be carried out under the same or similar conditions as described hereinabove for cyclisation since the compound of formula (II) or (III), or the corresponding open-chain precursor of the compound of formula (IV), need not be isolated but may be cyclised in situ, for example by a method analogous those described by A. Pernot and A. Willemart in Memoires Presentes a La Soc. Chim. 324 (1953); W. R. Schleigh, A. Catala and F. D. Popp in J. Het. Chem., 2, 379 (1965); or I Badilescu in Tetrahedron, 26 4207 (1970).

(3) A further method comprises hydrolysis of 1-(1,3-benzodioxol-5-yl)-2-imino-pyrrolidine (formula (VI)):

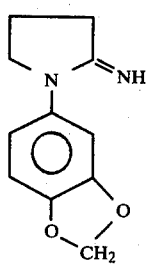
(VI)

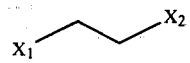
(XI)

wherein $X_1$ and $X_2$ may be the same or different and are defined as X in method (1) hereinabove.

The following Examples are provided by the way of illustration of the present invention and should in no way be construed as a limitation thereof. All temperatures indicated are in degrees Celsius.

The hydrolysis may be effected by standard hydrolysing agents known to those skilled in the art, for example, by adding a few drops of water or dilute aqueous acid to the compound.

The compound of formula (VI) may itself be prepared according to the method described by Kwok et al. in J. Org. Chem. (1967) 32, 738.

(4) A further method comprises a displacement reaction between a compound of formula (VII) and the pyrrolidinone anion formula (VIII):

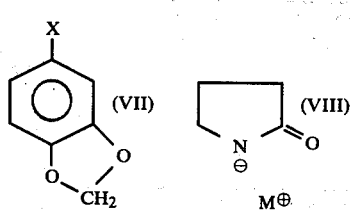

wherein X is a standard leaving group such as those hereinbefore described and M+ is an alkali metal or alkaline earth metal cation such as Na+.

(5) Another method comprises reacting 3,4-(methylenedioxy)aniline with γ-butyrolactone.

(6) Another method of preparation of compound (I) comprises the reaction the compound of formula IX by standard literature methods such as treatment with methylene sulfate or a dihalomethane (such as diiodomethane) with a suitable base such as potassium carbonate. The compound of formula IX can be prepared by reacting 3,4-dihydroxyl aniline (with the hydroxy groups protected) by the method described in method (1) or (5) above (followed by deprotection of the hydroxy groups) to form the pyrrolidinone.

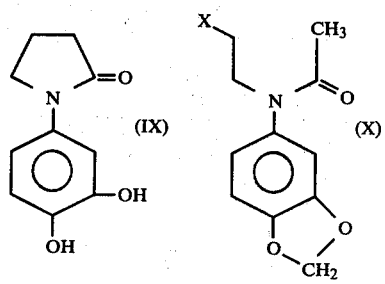

(7) Yet another preparation of compound I consists of subjecting a compound of formula (X) (where in X is as defined in method (1) above) to ring closure conditions similar to those described in method (1) above. Compounds of formula X can be prepared by reacting 3,4-(methlenedioxy)aniline with a compound of formula XI followed by acylation of the nitrogen by standard methods.

Example 1: Preparation of 1-(1,3-Benzodioxol-5-yl)-2-pyrrolidinone

Method A.

A mixture of 3,4-(methylenedioxy)aniline (200 g, 1.46 mole) and γ-butyrolactone (225 ml) was heated (in a dry nitrogen atmosphere) with stirring in a 200° oil bath for 2 days. Product was isolated from the reaction mixture by distillation under reduced pressure (b.p. 156°, 33 μ). Product was filtered over Silica Gel 60 (Trade Name) eluting with ethylacetate. The eluant was concentrated and the crystalline product was collected and washed with ether and petroleum ether affording 1-(1,3-benzodioxol-5-yl)-2-pyrrolidinone (153.4 g; 51%), m.p. 89°–91° which was one spot on tlc analysis.

Elemental analysis: Calcd. for $C_{11}H_{11}NO_3$: C, 64.38%; H, 5.40%; N, 6.83%. Found: C, 64.30%; H, 5.33%; N, 6.81%.

Method B.

4-Chlorobutyryl chloride (1095.5 g, 7.77 mole) was added at 10°–25° C. to a mixture of 3,4-(methylenedioxy)aniline (1000.0 g, 7.29 mole), triethylamine (749.0 g, 7.40 mole) and methylene chloride (2500 mL). After stirring for 18 hours at ambient temperature ether was added and the butyramide intermediate was filtered then reslurried in water. The damp butyramide was combined with methylene chloride (10 L), 50% w/w aqueous sodium hydroxide (2000.0 g, 25.0 mole) and benzyltriethylammonium chloride (50.0 g, 0.22 mole). After stirring for 2.5 hours at ambient temperature the mixture was diluted with water and the aqueous layer was then separated. The methylene chloride layer was washed with water, decolorized with Darco G-60 and Filtrol #19, then vacuum concentrated. Ether was added to the concentrate. The mixture was chilled and the solids were collected and recrystallized from methylene chloride/ether giving 2245.0 g (75%).

Example 2: Analgesic Activity

A. Acetic Acid Writhing Test (AAWT)

Using the procedure described by Koster et al. in Fed. Proc. 18, 412 (1959) and Vinegar et al. in Handbook of Experimental Pharmcology, 50-2, ch. 26, Anti-inflammatory Drugs, Ed J R Vane and S H Ferreira (1978), the acetic acid writhing test was performed, using both the mouse and the rat, to demonstrate the mild analgesic activity of the compound (I). Comparative results are given in Table I.

TABLE I

| Results of the Acetic Acid Writhing Assay in the Rat | |
|---|---|
| Compound | $ED_{50}$ mg/kg, p.o. |
| Compound | 36 ± 7.1 |
| Acetaminophen | 127 ± 16.4 |
| Aspirin | 21 ± 3.4 |

TABLE I-continued

Results of the Acetic Acid Writhing Assay in the Rat

| Compound | ED$_{50}$ mg/kg, p.o. |
|---|---|
| Codeine Phosphate | 30 ± 2.7 |

B. Modified Trypsin Hyperalgesic Assay (THA)

This assay quantitatively measures analgesia and is designed to be unaffected by compounds possessing anti-inflammatory activity. The procedure described by Vinegar et al. in Eur. J. Pharmacol. 37, 23, (1976) was used to demonstrate the analgesic activity of the compound (I) and of certain known analgesics. The analgesic agents were administered 30 minutes after the administration of trypsin. In addition, a modification of Vinegar's published assay was carried out, comprising the administration of the analgesic agent preceding subplantar injection of trypsin (0.10 ml of 10% solution of trypsin in pyrogen-free water) by 15 minutes. In both THA's, pain scores were determined 60 minutes after trypsin injection. The result of the modification was to increase the sensitivity of the THA to the mild analgesic action of the agents. The comparative results are given in Table II.

TABLE II

Results of the Modified Trypsin Hyperalgesic Assay in the Rat

| | ED$_{50}$ mg/kg, p.o. | |
|---|---|---|
| Compound | 6.0 kg Force | 7.5 kg Force |
| Compound I | 24 ± 5.3 | 23 ± 3.5 |
| Acetaminophen | 95 ± 17.2 | I @ 200 |
| Aspirin | I @ 180 | — |
| Codeine Phosphate | 10 ± 1.7 | 8.8 ± 2.77 |

I = inactive

There were usually 6 rats at each dose level and at least 3 dose levels were used.

C. Rat Hot Plate Assay

The rat hot plate assay incorporated 2 modifications of the mouse hot plate assay originally described by Eddy et al., J. Pharmacol. Exp. Ther. 98, 121-137 (1950). The first modification was enlargement of the diameter of the cylindrical (water filled) copper plate to 25.0 cm to accommodate rats instead of mice. The second modification was the use of a temperature controller to regulate a 250 watt infrared heat lamp which was activated via a thermistor probe attached to the undersurface of the top of the copper plate. The surface temperature was thus maintained at 45±1.0° C. (N=28 measurements of the plate temperature under experimental conditions). The time in which a rat placed on the hotplate responded by lifting, shaking or licking either of its hind or forelimbs was recorded in tenths of a second. Only animals responding in pretest within 6-13 seconds were used in the studies. Drugs were suspended in 0.5% sodium carboxymethylcellulose and administered orally, by gavage, in a volume of 1.00 ml/100 g.b. wt. 60 min prior to testing. Animals which responded in less than 18.3 seconds were considered unprotected and those which did not respond within 18.3 seconds were considered protected. The reaction time of 18.3 seconds represented the sum of the mean pretest times of 40 untreated rats plus the time of 3 standard deviations of the mean. ED$_{50}$'s and their standard errors were estimated from a graph of the dose-response curves using the method of Miller and Tainter (Proc. Soc. Exp. Biol. Med. 57, 261-262 (1944). Following this procedure the analgesic activity of the compound (I) was compared to that of standard analgesic drugs (Table III).

TABLE III

Results of Hot Plate Assay

| Assay | Compound of Formula (I) | Aspirin | Acetaminophen | Codeine | Morphine |
|---|---|---|---|---|---|
| Hot Plate Assay - Rat ED$_{50}$ - mg/kg p.o. | 86 ± 16.5 | Inactive at 360 | Inactive at 360 | 57 ± 35.3 | 17 ± 3.6 |
| Hot plate Duration of Action* - Hrs (Dose - mg/kg, p.o.) | 5.0 (120) | — | — | 3.3 (90) | 2.5 (30) |

*Duration of Action in Rat Hot Plate assay represents the time in hrs to reduce 1.5 times the hot plate ED$_{50}$ to 40% inhibition.

Example 3: Acute Anti-Inflammatory Activity: Carrageenin Pleurisy Assay (CPA)

Following the procedure described by Vinegar et al. in Proc. Soc. Exp. Biol. Med. 151, 556, (1976), the acute anti-inflammatory activity of the compound (I) was compared with that of known anti-inflammatory drugs in the rat. The average 3 hour exudate volume for each drug-treated group was determined and the % inhibition relative to solvent-fed control animals calculated, the ED$_{50}$ being the dose required to reduce the 3 hour exudate volume by 50%.

TABLE IV

Results of Acute Anti-Inflammatory Activity Assay (CPA)
All Results Expressed as ED$_{50}$ mg/kg, p.o.

| Aspirin | 28 ± 3.2 |
|---|---|
| Acetaminophen | 172 ± 22.4 |
| Compound I | 48 ± 10.5 |

Example 4: Antipyretic Activity

The Yeast-Induced Hyperthermia Assay was used according to the procedure described by Khalili-Varasteh et al. in Arch. Int. Pharmacodyn. 219 149-159, (1976) to demonstrate the antipyretic activity of compound (I) and certain known antipyretics in the rat. The results are shown in Table V.

TABLE V

Results of Antipyretic Activity Assay
All results are expressed as $ED_{50}$ mg/kg

| Assay | Compound (I) | Aspirin | Acetaminophen |
|---|---|---|---|
| Rat Yeast Hyperthermia (p.o.) | 67 ± 4.2 | 50 ± 8.1 | 72 ± 8.6 |

Example 5: Pharmaceutical Formulations

| A. Capsule | |
|---|---|
| Ingredient | Amount per capsule (mg) |
| Compound I | 325.0 |
| Lactose | 174.0 |
| Corn Starch | 174.0 |
| Stearic Acid | 2.0 |

The finely ground active compound was mixed with the powdered excipients lactose, corn starch and stearic acid and packed into gelatin capsule.

| B. Tablet | |
|---|---|
| Ingredient | Amount per tablet (mg) |
| Compound I | 325.0 |
| Lactose | 125.0 |
| Corn Starch | 50.0 |
| Polyvinylpyrrolidone | 3.0 |
| Stearic acid | 1.0 |
| Magnesium stearate | 1.0 |
| TAMSP2-0/18/tc | |

The active compound was finely ground and intimately mixed with the powdered excipients lactose, corn starch, polyvinylpyrrolidone, magnesium stearate and stearic acid. The formulation was then compressed to afford one tablet weighing 250 mg.

| C. Suppository | |
|---|---|
| Ingredient | Amount per suppository |
| Compound I | 325.0 mg |
| Cocoa Butter, q.s. or Wecobee Base | 2.0 g |

Wecobee is the trade name of a hydrogenated carboxylic acid.

What is claimed is:

1. The compound of formula (I):

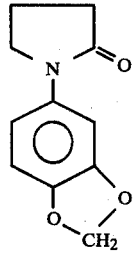

namely, 1-(1,3-benzodioxol-5-yl)-2-pyrrolidinone.

2. A pharmaceutical formulation comprising the compound 1-(1,3-benzodioxol-5-yl)-2-pyrrolidinone together with a pharmaceutically acceptable carrier therefor.

3. A formulation according to claim 2, selected from a capsule, tablet or suppository.

4. A method for treatment or prophylaxis of pain in a mammal comprising the administration to said mammal of a non-toxic, effective analgesic amount of the compound 1-(1,3-benzodioxol-5-yl)-2-pyrrolidinone.

5. A method for treatment or prophylaxis of pyresis in a mammal comprising the administration to said mammal of a non-toxic, effective antipyretic amount of the compound 1-(1,3-benzodioxol-5-yl)-2-pyrrolidinone.

6. A method for treatment or prophylaxis of inflammation in a mammal comprising the administration to said mammal of a non-toxic, effective anti-inflammatory amount 1-(1,3-benzodioxol-5-yl)-2-pyrrolidinone.

7. A method according to any of the claims 4, 5, or 6, which comprises the administration to said mammal of from 1 to 120 mg/kg body weight of the compound per day.

8. A method according to any of the claims 4, 5 or 6 which comprises the administration to said mammal of 15 mg/kg body weight per day of the compound.

9. The method of claim 4 in which the mammal is a human.

10. The method of claim 9 in which the compound is administered in a capsule, tablet or suppository.

11. The method of claim 5 in which the mammal is a human.

12. The method of claim 11 in which the compound is administered in a capsule, tablet or suppository.

13. The method of claim 6 in which the mammal is a human.

14. The method of claim 13 in which the compound is administered in a capsule, tablet or suppository.

15. The formulation of claim 2 in a form for oral, rectal or parenteral administration.

16. The formulation of claim 15 in the form of a syrup.

* * * * *

UNITED STATES PATENT AND TRADEMARK OFFICE
CERTIFICATE OF CORRECTION

PATENT NO. : 4,431,662
DATED : Feb. 14, 1984
INVENTOR(S) : Gordon L. Hodgson, Jr.

It is certified that error appears in the above—identified patent and that said Letters Patent is hereby corrected as shown below:

Column 9, line 36: Please delete "TAMSP2-0/18/tc"

Signed and Sealed this

Thirtieth Day of October 1984

[SEAL]

Attest:

GERALD J. MOSSINGHOFF

Attesting Officer

Commissioner of Patents and Trademarks